United States Patent [19]
Knifton

[11] Patent Number: 5,352,847
[45] Date of Patent: Oct. 4, 1994

[54] ONE-STEP SYNTHESIS OF METHYL T-BUTYL ETHER FROM T-BUTANOL USING PILLARED, PHOSPHATED MONTMORILLONITE CLAY CATALYSTS

[75] Inventor: John F. Knifton, Austin, Tex.

[73] Assignee: Texaco Inc., White Plains, N.Y.

[21] Appl. No.: 126,591

[22] Filed: Sep. 27, 1993

[51] Int. Cl.$^5$ .............................................. C07C 41/09
[52] U.S. Cl. ..................................................... 568/698
[58] Field of Search ......................................... 568/698

[56] References Cited

U.S. PATENT DOCUMENTS 5,099,072  3/1992  Knifton ............................... 568/698

Primary Examiner—Howard T. Mars
Attorney, Agent, or Firm—James L. Bailey; Kenneth R. Priem; Cynthia L. Kendrick

[57] ABSTRACT

A method is disclosed wherein t-butanol is reacted with methanol in a reaction zone in one step to provide methyl tert-butyl ether and the improvement of accomplishing the reaction which comprises:
a. Using a catalyst comprising a chlorohydrol-treated, phosphated montmorillonite clay,
b. continuously contacting said t-butanol and methanol in a molar amount of about 0.1 to 10 moles of methanol per mole of t-butanol with said catalyst at a temperature of about 20° C. to about 250° C. and a pressure of about atmospheric to about 1000 psig to obtain the methyl tert-butyl ether product.

16 Claims, 1 Drawing Sheet

ONE-STEP SYNTHESIS OF METHYL T-BUTYL ETHER FROM T-BUTANOL USING PILLARED, PHOSPHATED MONTMORILLONITE CLAY CATALYSTS

CROSS-REFERENCE

This application is related to U.S. Pat. Nos. 4,822,921; 4,827,048; 5,059,725; 5,157,162; 5,157,161; 5,214,218; and 5,183,947.

This invention concerns an improved process for preparing methyl tertiary-butyl ether (MTBE) by the reaction of tertiary-butanol and methanol in the presence of a catalyst comprising a chlorohydrol-treated, phosphated montmorillonite clay catalyst. MTBE has been generated in up to 40% concentration in the crude product. This catalyst demonstrates improved yields of MTBE product compared with unmodified montmorillonite clay. Another desirable feature is that the product mix separates into an isobutylene-MTBE product-rich phase and a heavier aqueous methanol phase at operating temperatures of 160° C. or greater.

BACKGROUND OF THE INVENTION

It is well-known that there is pressure to eliminate lead compounds from fuels for reasons of public health and environmental protection. Although the specifications for reformulated gasolines set by EPA will come into force in 1995, standards were brought into force on Nov. 1, 1992 requiring gasoline contain 2.7 wt % oxygen during the winter in nonattainment areas of the U.S. If the federal air quality standard for CO has not been achieved by a specified attainment date, the minimum oxygen content will increase to 3.1%. Moreover, starting in the summer of 1992, the maximum blending Reid vapor pressure (BRvp) of all gasolines is set at 9.0 psi. Since oxygenates are not only used as gasoline blending components, extenders, octane boosters and as key ingredients for reducing the emissions of CO and VOCs (Volatile Organic Compounds), it is expected that the demand for oxygenates will increase enormously in the coming years. See F. Cunill, et al., "Effect of Water Presence on Methyl tert-Butyl Ether and Ethyl tert-Butyl Ether Liquid-Phase Synthesis". Ind. Eng. Chem. Res. 1993, 32, 564–569.

Of all oxygenates, the tertiary ethers, such as methyl t-butyl ether (MTBE), ethyl tert-butyl ether (ETBE), and tert-amyl methyl ether (TAME) are preferred by refineries to lighter alcohols. They have lower blending Ried vapor pressure (BRvp), lower vaporization latent heats and low solubilities in water. The most common ether in use today is MTBE with a production of about 25 million metric tons. However, ETBE is becoming more attractive as the price of methanol goes up in relation to gasoline. It can be produced from renewable ethanol, in contrast to methanol derived from natural gas, and its use would help mitigate the greenhouse effect, Ibid., p. 564.

In addition, ETBE outranks MTBE as an octane enhancer and its BRvp is only 4 psi, which makes it more attractive for BRvp blends less than 8 psi required in some places during the summer. Therefore, a number of U.S. states and European countries are planning to make ETBE from bioethanol, Ibid.

At the present time, TAME, which is usually produced in MTBE refinery units when C5 olefins are diverted into the feed, is not viewed as rivaling MTBE or ETBE, Ibid.

The main drawback of tertiary ethers, is that they substantially increase aldehyde emissions which are under EPA regulations and have to decrease 15% by 1995. It is believed this drawback could be largely circumvented by mixing the tertiary ethers with tertiary alcohols. Tertiary butyl alcohol (tBA) has a very low atmospheric reactivity and low aldehyde emissions, since no hydrogens are contained in the carbon link to the oxygen. Basis experience acquired with tBA during the 1970s, a gasoline blended with a mixture of ethers and tBA and/or tertiary amyl alcohol should be shippable, Ibid.

Currently all commercial processes for the manufacture of methyl tert-butyl ether are based upon the liquid-phase reaction of isobutylene and methanol (Eq. 1), catalyzed by a cationic ion-exchange resin (see, for example: Hydrocarbon Processing, October 1984, p. 63; Oil and Gas J., Jan. 1, 1979, p. 76; Chem. Economics Handbook-SRI, September 1986, p. 543-7051P). The cationic ion-exchange resins used in MTBE synthesis normally have the sulphonic acid functionality (see: J. Tejero, J. Mol. Catal., 42 (1987) 257; C. Subramamam et al., Can. J. Chem. Eng., 65 (1987) 613).

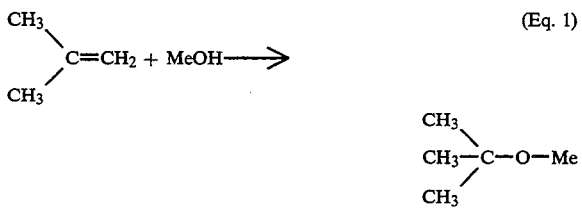

(Eq. 1)

With the expanding use of MTBE as an acceptable gasoline additive, a growing problem is the availability of raw materials. Historically, the critical raw material is isobutylene (Oil and Gas J., Jun. 8, 1987, p. 55). It would be advantageous, therefore, to have a process to make MTBE that does not require isobutylene as a building block. It would be advantageous to have an efficient process for making MTBE by reaction of methanol with tertiary-butyl alcohol, since t-butanol (tBA) is readily available commercially through isobutane oxidation.

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl. Vses Konf., 1977, 150 (C. A. 92:58165y). Here the tBA and methanol undergo etherification over KU-2 strongly acidic sulfopolystyrene cation-exchangers under mild conditions. This reference contains data on basic parameters of such a process. It is also pointed out that, although a plant for etherification over cation exchangers does not present any major problems, considerations include the fact that recycling large amounts of tert-butyl alcohol and methanol, as well as isobutylene, causes the scheme to be somewhat more expensive. Also, the progress of the reaction over cation exchangers is usually complicated by various adsorption and diffusion factors, by swelling phenomena, and by the variable distribution of the components between the solution and ion-exchanger phase. Furthermore, said acidic cation-exchangers with an organic (polystyrene or polymethacrylate) backbone generally have a very limited stability range with regard to operating temperatures, with temperatures above 120° C. normally leading to irreversible destruction of the resin and loss of catalytic activity.

In U. S. Pat. No. 2,282,469 to Frolich there is disclosed a process for preparing methyl tertiary-butyl ether over a catalyst comprising Kieselguhr impregnated with phosphoric acid at a temperature of about 175° F. to 350° F.

In U.S. Pat. No. 4,925,989 (1990), to Hagan et al., there is disclosed a process for preparing methyl tertiary-butyl ether wherein tertiary-butyl alcohol, isobutylene and methanol are continuously fed into a combination reactor distillation tower having a packed sulfonic acid resin catalyst bed where MTBE is produced.

G. B. Pat. No. 2,179,563 (1987) discloses the use of modified layered clay catalysts in reactions capable of catalysis by protons. Of particular interest in this invention were the three-layer sheet types, such as smectites, micas and vermiculites composed of successive layers of tetrahedral silica, octahedral alumina and tetrahedral silica which can exhibit swelling properties.

U.S. Pat. No. 4,590,294 (1986) discloses a process for the production of an ester comprising reacting an olefin from the group consisting of ethylene, hex-1-ene, hept-1-ene, oct-1-ene, 4-methylpent-1-ene, hex-2-ene, 1,5-hexadiene and cyclohexene with a carboxylic acid using as a catalyst component a hydrogen ion-exchanged layered clay. This reference would not seem to suggest a method for simultaneous dehydration of tert-butanol to isobutylene and the reaction with methanol to produce MTBE.

U.S. Pat. No. 4,822,921 (1989), To Texaco Chemical Co., discloses a method for preparing alkyl tertiary alkyl ethers which comprises reacting a $C_1$–$C_6$ primary alcohol with a $C_4$–$C_{10}$ tertiary alcohol over a catalyst comprising an inert support impregnated with phosphoric acid.

U.S. Pat. No. 5,099,072 (1992), to Texaco Chemical Co., discloses the reaction of t-butanol and methanol, or other $C_1$–$C_6$ primary alcohols and $C_4$–$C_{10}$ tertiary alcohols, in the presence of acidic montmorillonite clay catalysts having certain identifiable physical parameters, such as surface area, acidity range and moisture content.

In U.S. Pat. No. 5,059,725 (1991), to Texaco Chemical Co., a one-step synthesis for MTBE is disclosed wherein butanol and methanol are reacted over a catalyst comprising ammonium sulfate or sulfuric acid deposited upon a Group IV oxide. Again, other $C_1$–$C_6$ alcohols and $C_4$–$C_{10}$ tertiary alcohols will also work.

U.S. Pat. No. 5,157,162 (1992), to Texaco Chemical Co., discloses a fluorosulfonic acid-modified clay catalyst for the production of aliphatic ethers from $C_1$–$C_6$ primary alcohols and $C_4$–$C_{10}$ tertiary alcohols.

In U.S. Pat. No. 5,157,161 (1992), to Texaco Chemical Co., there is disclosed the use of a hydrogen fluoride-modified montmorillonite clay catalyst for producing alkyl-tertiary alkyl ethers.

U.S. Pat. No. 5,214,218 (1993), to Texaco Chemical Co., discloses a method for producing methyl t-butyl ether or other alkyl tertiary alkyl ethers using a catalyst comprising a montmorillonite clay treated with a haloacid.

It is known in the art to use pillared clays as catalysts in certain processes. Chem. Systems Topical Reports, Vol. II, 1986, Program, p. 61 (May 1987). Also see: European Patent Application 0083970A1 (Jul. 20, 1983) to British Petroleum.

Possible applications for pillared clays include catalytic cracking and olefin oligomerization and the reaction of alkylene oxides with alcohols. Chem. Systems, supra, p. 62.

Other reactions catalyzed by pillared clays include the hydration of olefins to alcohols and the reaction of olefins with acids to form esters. The clays can also be used in Friedel Crafts-type reactions.

There is a review of the use of pillared, cation-exchanged and acid-treated montmorillonite as catalysts for certain organic reactions by J. M. Adams et al., J. Inclusion Phenomena, 5, 663 (1987), and in Applied Clay Science, 2, 309 (1987). These clays display Bronsted and Lewis acid activities. It is noted that, while some cationic species are stable in solution over a wide concentration and pH range, others are not, particularly solutions containing aluminum. It is noted that it is difficult to ensure a reproducible $Al^{3+}$ clay and moreover, since workers have used slightly different exchanging and washing procedures, a comparison between related experiments is hindered. Commercial acid-treatment is carried out using concentrated hydrochloric, sulphonic or phosphoric acids. The concentration of the acid and the time of the treatment is variable. Sometimes the excess acid is removed by washing, whereas in other products this is not the case. Therefore there is a great variety in the type and activity of acid-treated clays.

With the current interest in the production of MTBE as a blending component in high octane gasoline, the identification of catalysts which provide substantial yields and extended life is important in the art. A catalyst which provides substantial yields, permits the production of MTBE in one step and incorporates the added feature of phase separation of the product above a certain temperature should contribute substantially to the art.

SUMMARY OF THE INVENTION

In accordance with certain of its aspects, the novel method of this invention for preparing methyl tert-butyl ether from tertiary-butyl alcohol (t-butanol) and methanol in one-step comprises reacting tertiary-butyl alcohol and methanol in the presence of a catalyst comprising a chlorohydrol-treated, phosphated montmorillonite clay at an elevated temperature and moderate pressure. Examples demonstrate particularly the effectiveness of acidic montmorillonite clays which have been pillared with chlorohydrol and treated with phosphoric acid.

DETAILED DESCRIPTION OF THE DRAWING

Figure 1:
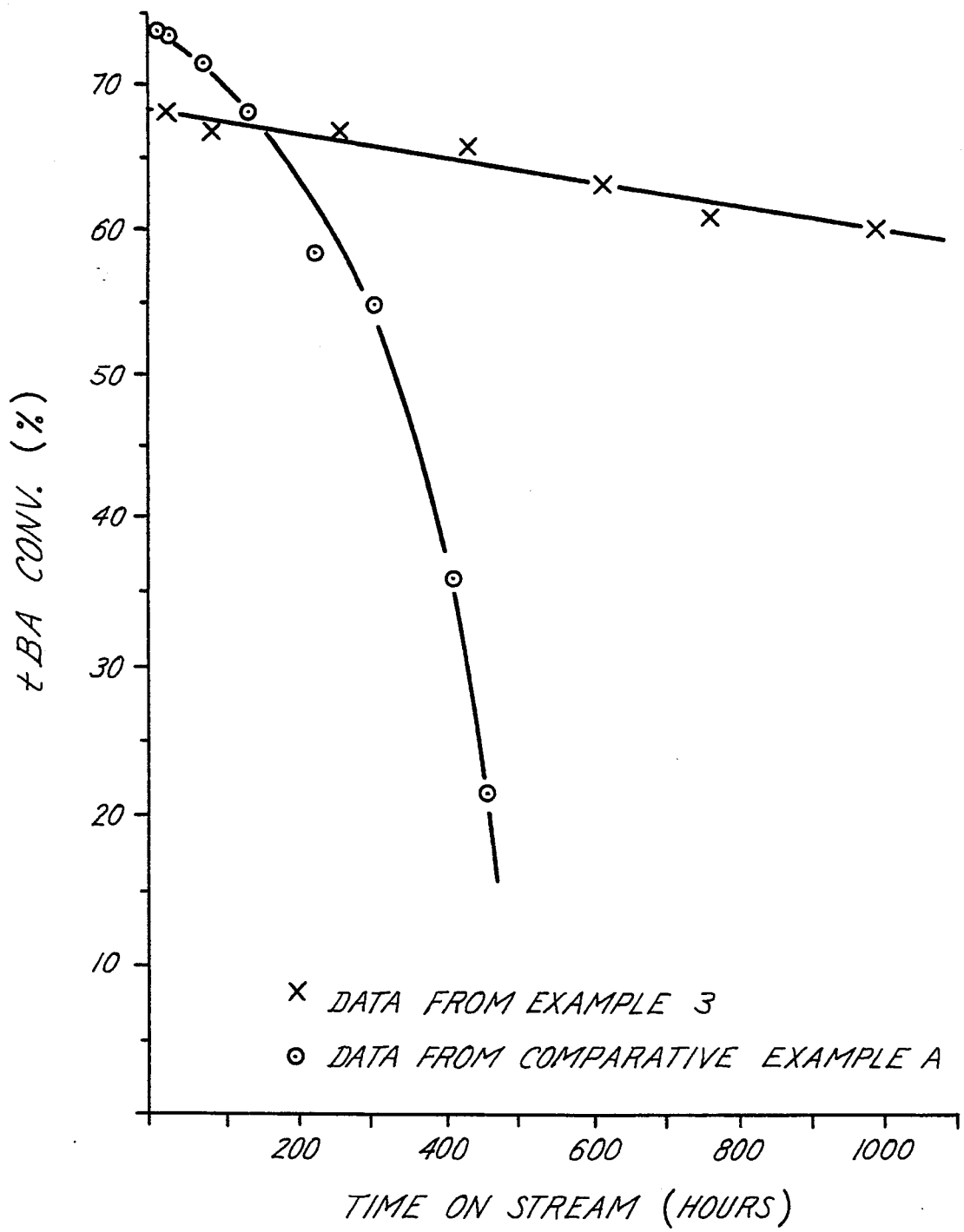

FIG. 1 represents a comparison of data from Example 3 and Table 2, using the modified clay of Example 1, with the untreated clay of Comparative Example A over a period of 1000 hours.

DESCRIPTION OF THE INVENTION

Preparation of the product of this invention may be carried out typically by reacting tertiary-butyl alcohol and methanol in the presence of an etherification catalyst. The etherification is carried out in one step and the catalyst comprises a chlorohydrol-treated, phosphated montmorillonite clay.

The reaction can be represented by the following:

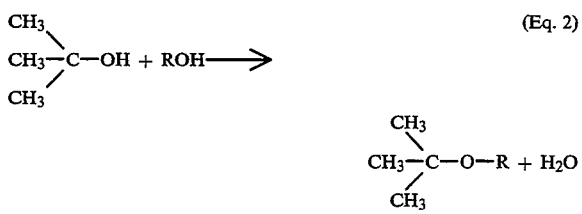

(Eq. 2)

where R is an alkyl group having 1 to 6 carbons.

Generally the methanol and t-butanol coreactants may be mixed in any proportion in order to generate the desired methyl t-butyl ether, but preferably the molar ratio of methanol to t-butanol in the feed mixture should be between 10:1 and 1:10, if the yield of desired MTBE is to be maximized. In order to achieve maximum selectivity to MTBE, and optimum conversion per pass, an excess of methanol in the liquid feed is desirable. The most preferred methanol-to-tertiary-butanol molar ratio is from 1:1 to 5:1. Optionally, said t-butanol plus methanol feed mixtures may be crude feedstocks containing other components, including water, ketones such as acetone, other alcohols such as 2-propanol, peroxides such as di-t-butyl peroxide, t-butyl hydroperoxide and allyl t-butyl peroxide, esters such as t-butyl formate, as well as methyl t-butyl ether product.

In certain circumstances, it may be particularly desirable that the tBA conversion be high enough (e.g. >40% per pass), such that the crude product mix phase separates into an isobutylene-MTBE product-rich phase and a heavier aqueous methanol phase. Preferably such a product phase separation would be achieved at as low an etherification temperature as possible, but particularly in the range 160°-200° C.

The same process may also be applied to the preparation of other alkyl tertiary alkyl ethers. For example, said process may be applied to the reaction of a $C_1$-$C_6$ primary alcohol such as methanol, ethanol, n-propanol and n-hexanol with a $C_4$-$C_{10}$ tertiary alcohol such as, for example, tertiary-butanol and tertiary amyl alcohol. Reaction of ethanol with tertiary-butanol would yield ethyl tertiary butyl ether (ETBE). Reaction of methanol with tertiary amyl alcohol (2-methyl-2-butanol) would then yield tertiary amyl methyl ether (TAME). Alternatively a mixture of alcohols, e.g., a mixture of $C_1$-$C_5$ alcohols, could be reacted to give a mixture of alkyl tert-alkyl ethers.

Good results were realized using certain treated smectite clays as catalysts for the reaction in Eq. 2, particularly Engelhard Grade 24 montmorillonite clays which have been pillared with chlorohydrol and treated with phosphoric acid.

The clays used to form this catalyst are silica-alumina clays. Chemically, clays are composed primarily of silicon, aluminum and oxygen, with minor amounts of magnesium and iron in some cases. Variations in the ratios of these constituents, and their crystal lattice configurations, result in some fifty separate clays, each with its own characteristic properties.

Particularly effective in reaction (Eq. 2) are smectite clays. Smectite clays are discussed in the article cited in Chem. Systems Report, 84-3. These clays have small particle size and unusual intercalation properties which afford them high surface area. They are alumino silicates with a unique structure that permits modifications which provide useful catalysts. They comprise layered sheets of octahedral sites between sheets of tetrahedral sites, where the distance between the layers can be adjusted by swelling. This layering is illustrated in an article by F. Figueras, Catal. Rev.-Sci. Eng., 30, 457 (1988). What renders the smectites of interest among the clay minerals is the combination of cation exchange, intercalation, and the fact that the distance between the layers can be adjusted by treatment with the appropriate solvent etc.

The three layered sheet types include montmorillonite, vermiculite and some brittle mica. The idealized basic structure of clays of this type is that of a pyrophyllite which has the basic formula $Si_8Al_4O_{20}(OH)_4$.

A general representation of the montmorillonite structure is:

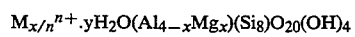

Where:
M represents the interlamellar (balancing cations), normally sodium or lithium and x, y and n are integers.

The value of x depends on the origin of the mineral.

Pillared or intercalated clays are similar to zeolites in many respects. They have ion-exchange capacity. The layers are held apart by metal ions or metal-containing cations that can be conceived of as "pillars" which are inserted by ion-exchange reactions. Between the layers are cavities in which catalyzed chemical reactions take place.

Suitable smectite clays for pillaring are acidic montmorillonite clays. Acids, including mineral acids such as sulfuric acid and phosphoric acid, activate montmorillonites by attacking and solubilizing structural cations in the octahedral layers. This opens up the clay structure and increases surface area. Preferably these acid clays should have acidities in the range of 0.1 to 30, or greater, mg KOH/gm, titrated to a phenolphthalein end point. Their surface area should be >30 m²/g, and preferably 100 to 1000 m²/g. Their moisture content should also be limited, which can be accomplished by heating to about 220° F., by which method the weight loss is generally less than 20 wt %.

Specific examples of suitable montmorillonite clays for pillaring include Engelhard's Filtrol Grade 113 powder, having a residual acidity of 10 mg KOH/gm, a surface area of 300 m²/g, and a moisture content of 4 wt %; Filtrol Grade 13 powder, having an acidity of 15 mg KOH/g, a surface area of 300 m²/g, and a moisture content of 16 wt %; Filtrol Grade 24 granules of particle size 20/60 mesh, having an acidity of 16 mg KOH/g, a surface area of 300 m²/g and a moisture content of 10 wt %; granular Filtrol Grade 224, of particle size 20/60, having an acidity of 3.0 mg KOH/g, a surface area of 350 m²/g and a moisture content of <1 wt %; as well as extruded Filtrol Grade 62 which may be in 1/16" or 3/16" diameter extrudates and have an acidity of ca. 3.0 mg KOH/g.

In order to obtain the pillared catalyst, said montmorillonite clays are preferably treated with a chlorohydrol compound as demonstrated in Example 1. The pillared clay was prepared from Engelhard Grade 24, previously treated with mineral acid such as sulfuric acid, by adding it to a vigorously stirred solution of an equal amount of aluminum chlorohydrate solution in distilled water. Chlorohydrol is also known as aluminum chlorohydrate and is made by reacting aqueous aluminum chloride with metallic aluminum (see J. R.

Butrville and T. J. Pinnavaia, "Characterization of Catalytic Materials", Chap. 8, p. 151, 1992).

The phosphorous impregnated on the catalyst in the instant invention should be present as a phosphoric acid or fluorophosphoric acid group which is chemically bound to the titania support. In the latter case, the exact nature of the bonding is not fully understood, but is believed to include, for the fluorophosphoric acid-on-titania catalyst, the following:

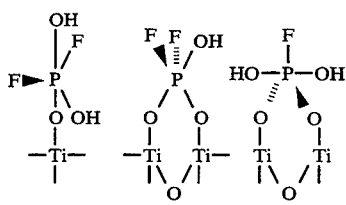

Said phosphorous may be introduced onto the clay as phosphoric acid, $H_3PO_4$, as polyphosphoric acid and phosphorous acid, as well as phosphoryl halides such as phosphoryl chloride, $POCl_3$, or phosphoryl fluoride. The same phosphorous may also be introduced as a substituted phosphoric acid, such as a fluorophosphoric acid, including fluorophosphoric acid, $FPO_3H_2$ and difluorophosphoric acid $F_2PO_2H$. Also effective are alkylphosphonic acids such as methylphosphonic acid and ethylphosphonic acids, alkylphosphonic halides, such as ethylphosphonic dichloride and methylphosphonic fluoride, together with certain phosphates and phosphites including trimethylphosphite, diphenylphosphite, triethylphosphite, tributylphosphate, diphenylphosphate, and diethylbenzylphosphate, and certain phosphonates such as triethylphosphonate, diethyl-n-heptylphosphonate, hexafluorophosphate, and di-n-octylphenylphosphonate. Ammonium hydrogen phosphates, including diammonium hydrogen phosphate, are also effective as phosphorous sources in the practice of this invention.

Mixtures of the phosphorous-containing compounds listed above may also be employed in the formulated catalyst.

A solution of about 50% to 100% and preferably about 60% to 90% phosphorous compound is used to phosphate the acidic montmorillonite granules or extrudates. Said phosphorous compounds may be introduced into the inert support in a liquid or gaseous form, in the presence, or absence, of an inert diluent. The resulting phosphated granules are washed until no phosphorous can be detected in the filtrate. The phosphorous content of the granules should be between about 0.01% and 10% and preferably 1% to 4%, although concentrations outside this range may also be employed. The acidity should be between 0.01 mq KOH/g and 10 mq KOH/g and preferably 1 to 4 mq KOH/g.

As Example 1 indicates a suitable amount is about 2.5-3.5 wt %.

The montmorillonite clays to be modified may be in the form of powders, pellets, granules, spheres, shapes and extrudates. The examples described herein demonstrate certain advantages using granules. An example of a commercially-available, montmorillonite clay which can be treated with a phosphoric acid is Engelhard Grade 24 granules.

It has been discovered that chlorohydrol-treated phosphated clays possess a number of desirable properties for the production of MTBE. FIG. 1 demonstrates the excellent activity and life of the modified catalyst over 1000 hours compared with the unmodified catalyst of Comparative Example A.

The reaction may be carried out in either a stirred slurry reactor or in a fixed bed continuous flow reactor. The catalyst concentration should be sufficient to provide the desired catalytic effect.

Etherification can generally be conducted at temperatures from 20° to 250° C.; the preferred range is 80° to 200° C. As mentioned, at temperature of 160° C. or greater two phases are observed in the product. The total operating pressure may be from 0 to 1000 psig, or higher. The preferred pressure range is 50 to 500 psig.

Typically, MTBE is generated continuously in up to about 40 wt % concentration in the crude liquid product at total liquid hourly space velocities (LHSV) of up to 5 or higher and relatively mild conditions, where:

$$LHSV = \frac{\text{Volume Of Total Liquid Feed Run Through The Reactor Per Hour}}{\text{Volume Of Catalyst In Reactor}}$$

Conversions of t-butanol (tBA, wt %) are estimated in the following examples using the equation:

$$\frac{(\text{Wt \% Conc. of tBA in Feed} - \text{Wt \% Conc. of tBA in Product})}{\text{Wt \% Conc. of tBA in Feed}} \times 100$$

Selectivities of methyl t-butyl ether (MTBE, mole %) and isobutylene ($C_4H_8$, mole %) are estimated from:

$$\frac{\text{Moles of MTBE (or } C_4H_8\text{) in Product}}{\text{moles of tBA converted}} \times 100$$

The examples which follow illustrate the one-step synthesis of MTBE from tBA and MeOH (Eq. 2) using chlorohydrol-treated, phosphated acidic montmorillonite granules. The examples are only intended as a means of illustration and it is understood the invention is not meant to be limited thereby.

The examples illustrate:

1) Example 1 illustrates the preparation of an acidic montmorillonite clay which has been pillared with chlorohydrol and treated with phosphoric acid.

2) In Example 2 the modified clay of Example 1 gave excellent etherification activity in continuous unit equipment with ca. 40 wt % concentration of MTBE in the product effluent for a 1.1:1 MeOH/tBA feedstock, at LHSV 2, 120° C. operating temperature, plus product phase separation at 160° C. and higher into an isobutylene-MTBE product-rich phase and an aqueous methanol heavier phase (see Table 1).

3) In Example 3, Table 2 and FIG. 1, the same modified clay of Example 1 gave excellent activity and life over 1000 hours using a crude 2:1 MeOH/tBA feedstock also containing acetone ($Ac_2O$), isopropanol (2-PrOH), MTBE, water, t-butyl formate (TBF), and di-t-butyl peroxide (DTBP).

4) In comparison run A, with untreated, acidic clay catalyst, said clay shows similar initial activity but a rapid decline in performance over 400 plus hours (See Table 3 and FIG. 1).

EXAMPLE 1 (6798-2)

This example illustrates the preparation of a chlorohydrol-treated, phosphated montmorillonite clay.

To 100 g of granular montmorillonite clay that has previously been treated with sulfuric acid (Engelhard Grade 24, 20/60 mesh, acidity 16 mq KOH/g) was added a solution of 50% chlorohydrol (100 g) from Reheis Chemical Company in 2 liters of distilled water. The mixture was stirred at room temperature for 2 days and the solids filtered off, washed with distilled water until aluminum ions could no longer be detected in the filtrate and dried in air. Said material (95 g) was then treated with a solution of 85% phosphoric acid (11.5 g) in 1 liter of distilled water, the mixture stirred vigorously overnight and the phosphated solids recovered by filtration, washed with distilled water until phosphorous could no longer be detected in the filtrate and calcined at 300° C. for 3 hours.

The final white, granular product was found by analysis to have the following properties:

| | |
|---|---|
| Phosphorous Content | 2.9% |
| Water Content | 0.1% |
| Acidity | 1.7 mq KOH/g |

EXAMPLE 2 (6834-9)

This example illustrates the cosynthesis of MTBE and isobutylene from a t-butanol/methanol feedstock using a chlorohydrol-treated, phosphated clay.

Synthesis was conducted in a tubular reactor ($\frac{1}{2}''$ i.d., 12″ Long) constructed of 316 stainless steel, operated upflow and mounted in a furnace controllable to ±1.0° C. and fitted with pumps allowing flow control up to <±1 cc/hr. The reactor was also fitted with a pressure regulating device and equipment for monitoring temperature, pressure and flow rate.

The reactor was charged at the beginning of the experiment with 25 cc of the chlorohydrol-treated, phosphated, granular clay of Example 1 and a screen of glass wool placed at the top and bottom of the reactor to ensure the catalyst would remain in the middle portion. The catalyst bed was then treated with a 1.1:1 molar mix of methanol and t-butanol at a rate of 50 cc/hr, while the reactor was held at 120° C. with a total unit pressure of 300 psi. Samples of effluent were collected in duplicate and analyzed by glc and gc-ir.

Typical analyses data for samples taken under these conditions are summarized in Table 1. Performances at higher temperatures (160°, 180°, 200° C.) were similarly determined using the same procedures. These results are also given in Table 1. t-butanol conversion levels and MTBE/isobutylene molar selectivities were as follows:

| SAMPLE | OPERATING TEMP (°C.) | tBA CONC. (%) | MOLAR SELECTIVITY (%) | |
|---|---|---|---|---|
| | | | ISOBUTYLENE | MTBE |
| 1 | 120 | 67 | 23 | 76 |
| 3 | 140 | 71 | 33 | 63 |
| 8 | 180 | 94 | a | a | aNot Determined

TABLE 1

MTBE FROM MeOH/tBA - CH + H₃PO₄/CLAY 24

| Ex. | Catalyst | MeOH/tBA Molar Ratio | Temp. (°C.) | Feed Rate (cc/hr) | Time On Stream (Days) | SAMPLE | ←PRODUCT COMPOSITION (WT %)→ | | | | |
|---|---|---|---|---|---|---|---|---|---|---|---|
| | | | | | | | H₂O | MeOH | C₄H₈ | tBA | MTBE |
| 2 | Ex. 1 | | | | | FS-1 | | 33.4 | | 66.1 | |
| | | 1.1:1 | 120 | 50 | 1 | 1 | 11.8 | 18.7 | 7.5 | 22.1 | 39.7 |
| | | | | | | 2 | 11.8 | 18.6 | 7.4 | 22.3 | 39.4 |
| | | | 140 | 50 | 2 | 3 | 12.7 | 21.3 | 11.7 | 19.1 | 34.9 |
| | | | | | | 4 | 12.8 | 21.3 | 11.7 | 19.2 | 34.7 |
| | | | 160 | 50 | 3 | 5 | 2.2 | 11.5 | 54.2 | 5.2 | 26.7 |
| | | | | | | | 32.1 | 48.4 | 4.8 | 6.8 | 7.5 |
| | | | | | | 6 | 2.3 | 11.5 | 54.9 | 4.9 | 26.2 |
| | | | | | | | 32.4 | 48.3 | 4.6 | 6.8 | 7.5 |
| | | | 180 | 50 | 4 | 7 | 0.8 | 9.1 | 71.9 | 2.4 | 15.0 |
| | | | | | | | 33.3 | 54.5 | 3.2 | 5.4 | 3.3 |
| | | | | | | 8 | 1.5 | 7.1 | 69.8 | 2.4 | 14.5 |
| | | | | | | | 33.1 | 55.7 | 3.1 | 4.9 | 2.9 |

EXAMPLE 3 (6834-87)

This example illustrates the cosynthesis of MTBE and isobutylene from a crude aqueous t-butanol/methanol feedstock using a chlorohydrol-treated phosphated, clay catalyst.

Using the equipment and following the procedures of Example 2, 25 cc of the chlorohydrol-treated, phosphated, granular clay of Example 1 was charged to the reactor system and treated with a crude 2:1 molar mixture of methanol and t-butanol containing sizable quantities of water, acetone (Ac₂O), isopropanol (2-PrOH), MTBE, t-butyl formate (TBF), and di-t-butyl peroxide (DTBP), at a temperature of 120° C. and a total feed rate of 50 cc/hr. Samples of effluent were collected periodically in stream and analyzed by glc. Typical analyses data are summarized in Table 2. The calculated t-butanol conversion levels and isobutylene/MTBE selectivities are as follows:

| SAMPLE | TIME ON STREAM (HRS.) | t-BUTANOL CONV. (%) | MOLAR SELECTIVITY (%) | |
|---|---|---|---|---|
| | | | ISOBUTYLENE | MTBE |
| 1 | 24 | 68 | 14 | 84 |
| 4 | 430 | 66 | 16 | 86 |
| 8 | 1000 | 60 | 17 | 86 |

A graphical plot of catalyst performance as measured by t-butanol conversion per pass-versus time on stream is illustrated in FIG. 1 (X-Data Points).

TABLE 2

MTBE FROM MeOH/tBA - CH + H3PO4/CLAY 24

| Ex. | Catalyst | MeOH/tBA Molar Ratio | Temp. (°C.) | LHSV | Time On Stream (Days) | SAMPLE | H2O | MeOH | C4H8 | AC2O | 2-PrOH | tBA | MTBE | DTBP | TBF |
|---|---|---|---|---|---|---|---|---|---|---|---|---|---|---|---|
| 3 | Ex. 1 | 2:1 | 120 | 2 | | FS-1 | 5.5 | 41.7 | | 0.6 | 1.5 | 48.8 | 2.0 | 4.8 | 0.18 |
| | | | | | 1 | →1 | 14.1 | 29.2 | 3.4 | 0.6 | 1.5 | 15.6 | 35.2 | 5.1 | — |
| | | | | | 4 | 2 | 13.9 | 29.1 | 3.4 | 0.6 | 1.5 | 15.9 | 35.6 | 5.2 | — |
| | | | | | 11 | 3 | 13.5 | 29.2 | 3.8 | 0.6 | 1.5 | 16.0 | 35.3 | 5.3 | — |
| | | | | | | FS-2 | 5.5 | 41.6 | | 0.6 | 1.5 | 49.1 | 1.7 | 4.8 | 0.18 |
| | | | | | 18 | →4 | 13.6 | 29.0 | 3.8 | 0.6 | 1.5 | 16.6 | 34.8 | 5.2 | — |
| | | | | | 26 | 5 | 13.3 | 29.7 | 3.8 | 0.6 | 1.5 | 18.0 | 33.1 | 5.5 | — |
| | | | | | | FS-3 | 5.3 | 39.6 | | 0.5 | 1.4 | 47.7 | 2.0 | 4.8 | 0.19 |
| | | | | | 32 | 6 | 13.3 | 30.1 | 3.7 | 0.5 | 1.5 | 18.8 | 32.1 | 5.3 | — |
| | | | | | 39 | 7 | 13.1 | 29.9 | 3.8 | 0.5 | 1.5 | 23.9 | 27.2 | 4.4 | — |
| | | | | | 42 | →8 | 13.4 | 30.2 | 3.8 | 0.6 | 1.5 | 19.2 | 31.3 | 5.0 | — |

COMPARATIVE EXAMPLE A (6707-74)

This example illustrated the cosynthesis of MTBE and isobutylene from a crude t-butanol/methanol feedstock using an untreated clay catalyst.

Using the equipment and following the procedures of Example 2, 25 cc of sulfuric acid-treated granular clay that had not been sequentially treated with chlorohydrol and phosphoric acid (Engelhard Grade 24 granules, 20/60 mesh) was charged to the reactor system and treated with a crude 2:1 molar mixture of methanol and t-butanol containing sizeable quantities of acetone, isopropanol, MTBE, t-butyl formate and di-t-butyl peroxide, at a temperature of 120° C. and a total feed rate of 50 cc/hr. Samples of effluent were collected periodically on stream and analyzed by glc. Typical analyses data are summarized in Table 3. The calculated t-butanol conversion levels and isobutylene/MTBE selectivities are as follows:

| SAMPLE | TIME ON STREAM (HRS) | t-BUTANOL CONV. (%) | MOLAR SELECTIVITY (%) ISOBUTYLENE | MTBE |
|---|---|---|---|---|
| 1 | 6 | 74 | 15 | 89 |
| 6 | 310 | 55 | 19 | 88 |
| 8 | 460 | 22 | a | a |

<sup>a</sup>Not Determined

A graphical plot of catalyst performance as measured by t-butanol conversion per pass-versus time on stream is illustrated in FIG. 1 (0-data points).

What is claimed is:

1. In a method wherein t-butanol is reacted with methanol in one-step in the presence of a catalyst to provide methyl tert-butyl ether (MTBE), the improvement comprising using as a catalyst a chlorohydrol-treated, phosphated acidic montmorillonite clay and continuously contacting said t-butanol and methanol in a molar amount of about 0.1 to 10 moles of methanol per mole of t-butanol with said catalyst at a temperature of 20° C. to 250° C. and a pressure of atmospheric to 1000 psig to obtain methyl tert-butyl ether product.

2. The method of claim 1 wherein said montmorillonite clay has the structure:

$$M_{x/n}{}^{n+} \cdot yH_2O(Al_{4-x}Mg_x)(Si_8)O_{20}(OH)_4$$

Where: M represents the interlamellar balancing cations, normally sodium or lithium and x, y and n are integers.

3. The method of claim 2 wherein the montmorillonite clay has been pretreated with sulfuric acid.

4. The method of claim 2 wherein the acidic montmorillonite clay is phosphated with a compound selected from the group consisting of phosphoric acid, polyphosphoric acid, phosphoryl halides, fluorophosphoric acid, difluorophosphoric acid, alkyl phosphonic acids and alkylphosphonic halides.

5. The method of claim 1 wherein the acidic montmorillonite clay is phosphated with phosphoric acid or polyphosphoric acid.

6. The method of claim 1 wherein the acidic montmorillonite clay is phosphated with phosphoric acid.

7. The method of claim 6 wherein the percent by weight of phosphorous in the catalyst is 0.01 to 10 wt %.

TABLE 3

MTBE FROM MeOH/tBA - CLAY 24

| Ex. | Catalyst | MeOH/tBA Molar Ratio | Temp. (°C.) | LHSV | Time On Stream (Days) | SAMPLE | H2O | MeOH | C4H8 | AC2O | 2-PrOH | tBA | MTBE | DTBP | TBF |
|---|---|---|---|---|---|---|---|---|---|---|---|---|---|---|---|
| A | Clay-24 | 2:1 | 120 | 2 | | FS-1 | | 41.0 | | 0.5 | 1.3 | 50.9 | 3.4 | 4.6 | 0.2 |
| | | | | | ½→ | 1 | 9.2 | 27.6 | 4.4 | 0.5 | 1.2 | 13.1 | 43.8 | 5.3 | 0.07 |
| | | | | | 1 | 2 | 9.0 | 27.7 | 4.2 | 0.5 | 1.3 | 13.5 | 43.7 | 5.4 | 0.09 |
| | | | | | 3 | 3 | 9.0 | 28.1 | 4.2 | 0.6 | 1.4 | 14.0 | 42.6 | 5.3 | 0.09 |
| | | | | | 6 | 4 | 8.6 | 28.5 | 4.3 | 0.7 | 1.4 | 16.5 | 39.9 | 5.3 | 0.08 |
| | | | | | 10 | 5 | 6.9 | 29.8 | 3.9 | 0.6 | 1.4 | 21.3 | 36.1 | 5.4 | 0.09 |
| | | | | | 13→ | 6 | 6.7 | 31.7 | 3.9 | 0.6 | 1.4 | 22.9 | 32.7 | 5.4 | 0.09 |
| | | | | | 17 | 7 | 4.4 | 35.4 | 2.9 | 0.6 | 1.4 | 32.8 | 22.6 | 5.3 | 0.07 |
| | | | | | 19→ | 8 | 2.7 | 37.8 | 2.0 | 0.6 | 1.4 | 39.8 | 15.6 | 5.4 | 0.04 |

8. The method of claim 7 wherein the percent by weight of phosphorous in the catalyst is 1-4 wt %.

9. The method of claim 1 wherein the etherification temperature is from 80° C. to 200° C.

10. The method of claim 2 wherein the clay is in granular form and has a particle size of 20/60 mesh.

11. The method of claim 3 wherein the clay has an acidity of 16 mg/KOH/g.

12. The method of claim 3 wherein the clay has a surface area of about 300 m²/g.

13. The method of claim 3 wherein the clay has a moisture content of about 10%.

14. The method of claim 1 wherein the operating temperature is in the range of 160° to 200° C. and the product comprises a two phase mix of an isobutylene-MTBE product-rich phase and a heavier aqueous methanol-rich phase.

15. In a method wherein a $C_1$-$C_6$ primary alcohol is reacted with a $C_4$-$C_{10}$ tertiary alcohol in the presence of a catalyst to provide alkyl tertiary alkyl ethers, the improvement comprising using as a catalyst a chlorohydrol-treated, phosphated acidic montmorillonite clay and continuously contacting said tertiary alcohol and primary alcohol in a molar amount of about 0.1 to 10 moles of methanol per mole of t-butanol with said catalyst at a temperature of 20° C. to 250° C. and a pressure of atmospheric to 1000 psig to obtain alkyl tertiary alkyl ethers.

16. The method of claim 15 where the primary alcohol is ethanol, the tertiary alcohol is tertiary butanol and the alkyl tertiary alkyl ether is ethyl tertiary butyl ether.

* * * * *